(12) United States Patent
Evans et al.

(10) Patent No.: US 8,025,631 B2
(45) Date of Patent: *Sep. 27, 2011

(54) WATER RESISTANT UNDERCAST LINER

(75) Inventors: John C. Evans, NR Rochdale (GB); Shitij Chabba, Charlotte, NC (US)

(73) Assignee: BSN Medical, Inc., Charlotte, NC (US)

( * ) Notice: Subject to any disclaimer, the term of this patent is extended or adjusted under 35 U.S.C. 154(b) by 75 days.

This patent is subject to a terminal disclaimer.

(21) Appl. No.: 12/091,090

(22) PCT Filed: Oct. 25, 2006

(86) PCT No.: PCT/US2006/060226
§ 371 (c)(1),
(2), (4) Date: Sep. 22, 2008

(87) PCT Pub. No.: WO2007/051122
PCT Pub. Date: May 3, 2007

(65) Prior Publication Data
US 2009/0177137 A1    Jul. 9, 2009

Related U.S. Application Data

(60) Provisional application No. 60/730,630, filed on Oct. 26, 2005.

(51) Int. Cl.
*A61F 5/00* (2006.01)
*A61L 15/00* (2006.01)
*D03D 3/02* (2006.01)
(52) U.S. Cl. .............. 602/6; 602/26; 602/76; 139/387
(58) Field of Classification Search ............... 602/6, 20, 602/21, 23, 26, 41, 43, 44, 45, 54, 62, 76; 139/383 B, 383 R, 387 R, 389 R, 390 R, 391–394, 403, 405, 408; 66/192–194, 196, 202

See application file for complete search history.

(56) References Cited

U.S. PATENT DOCUMENTS

| | | | |
|---|---|---|---|
| 5,256,134 A * | 10/1993 | Ingham | 602/8 |
| 5,277,954 A * | 1/1994 | Carpenter et al. | 428/71 |
| 5,380,260 A * | 1/1995 | Blott | 602/41 |
| 5,514,080 A | 5/1996 | Blott et al. | |
| 5,749,843 A * | 5/1998 | Miller | 602/75 |
| 2002/0104576 A1 | 8/2002 | Howland | |
| 2004/0113317 A1 * | 6/2004 | Healey et al. | 264/292 |
| 2005/0058673 A1 | 3/2005 | Scholz et al. | |
| 2009/0036812 A1 * | 2/2009 | Chabba et al. | 602/8 |

FOREIGN PATENT DOCUMENTS

| WO | W091/02551 A1 | 3/1991 |
| WO | W094/27648 A1 | 12/1994 |
| WO | WO 2005052235 A1 * | 6/2005 |

* cited by examiner

*Primary Examiner* — Patricia Bianco
*Assistant Examiner* — Ophelia Hawthorne
(74) *Attorney, Agent, or Firm* — Oliff & Berridge, PLC

(57) ABSTRACT

An undercast liner for being applied to an anatomical shape of a patient and overlaid with a cast material. An elongate fabric has two opposing faces and an intermediate spacer area that both separates and interconnects the opposed faces. The liner is constructed at least in part of hydrophobic, water resistant monofilament yarn for providing enhanced water resistance, light weight, breathability and resistance to collapse and degradation due to moisture and bacteria during extended use to the liner. The liner has sufficient stretch in both a length-wise and width-wise direction to facilitate conforming the undercast liner around the anatomical shape without wrinkling during application.

11 Claims, 8 Drawing Sheets

WATER RESISTANT UNDERCAST LINER

TECHNICAL FIELD AND BACKGROUND OF THE INVENTION

This invention relates to an undercast liner of the type used to protect and cushion the skin of a patient from the relatively rigid material of a cast, such as constructed of plaster of Paris or synthetic cast tape. The liner allows the patient to carry out routine activities such as bathing, showering, swimming and the like without fear of the liner getting wet.

Traditional cast padding is constructed from a simple stockinette and padding material made from cotton or synthetic fibers, and offers poor or no water resistant capability. Cotton and some synthetic paddings actually absorb and retain large quantities of water. A cast is typically worn for a period of 6-8 weeks. During this period of time, traditional casts having a water-absorbent stockinette can promote skin maceration, discomfort and breed bacteria-causing odor as perspiration and water from washing and bathing migrates to and through the stockinette. The stockinette remains wet or damp for an extended period of time, causing the problems mentioned above.

The present invention provides a more conformable, water-resistant liner at a reduced cost as compared to water resistant products already available in the market. The present invention is directed to a construction that overcomes the drawbacks of water-resistant undercast liners such as that found in U.S. Pat. Nos. 5,102,711 and 5,277,954. For example, the monofilament structure of the liner has higher elongation in the width direction and provides a higher stretch during application that results in a better conforming liner which can be easily molded around a limb. Due to the improved padding/cushioning as compared to other liner and padding products known in the prior art, the undercast liner of the present invention requires fewer layers during application. The present invention may also have an adhesive coating incorporated on either or both surfaces. The tacky surface, when applied away from the skin, adheres to itself sufficiently to form a smoother underlayer for a cast. Additionally, it provides a non-slip effect under the cast tape and keeps the liner in position to facilitate easier application of the cast tape.

One of the problems with conventional cast padding as well as commercially available water resistant padding is that the padding collapses underneath a cast over the duration of 4-6 weeks as water and perspiration are absorbed into the structure. This reduction in thickness and resultant increase in density retards moisture transfer by both wicking and evaporation, and lessens the protection offered by the padding.

A water-resistant undercast liner such as disclosed and claimed in this application can help alleviate skin maceration problems which generally require additional treatment or therapy and eliminates the need for frequent cast changes. The present invention accommodates bathing, showering and contact with water without significant penetration of water into the padding, therefore keeping the skin relatively dry. In addition, the padding of the present invention provides improved conformability, cushioning, breathability, ease of application and a low profile as compared to water-resistant products currently in the market.

SUMMARY OF THE INVENTION

Therefore, it is an object of the invention to provide a water resistant undercast liner.

It is another object of the invention to provide an undercast liner that is comfortable when worn under a plaster or synthetic cast tape cast.

It is another object of the invention to provide an undercast liner that is relatively thin and thus provides a low profile undercast liner layer when properly overlapped during application.

It is another object of the invention to provide an undercast liner that is relatively open and therefore breathable.

It is another object of the invention to provide an undercast liner that is resistant to collapse during extended use.

It is another object of the invention to provide an undercast liner that promotes drainage of water from the cast/liner if wetting does occur.

It is another object of the invention to provide an undercast liner that is highly resilient.

In accordance with one embodiment of the invention, an undercast liner for being applied to an anatomical shape of a patient and overlaid with a cast material is provided, and comprises an elongate fabric having two opposing faces and an intermediate spacer area that both separates and interconnects the opposed faces. The liner is constructed at least in part of hydrophobic, water resistant monofilament yarn for providing enhanced water resistance, light weight, breathability and resistance to collapse and degradation due to moisture and bacteria during extended use to the liner. The liner has sufficient stretch in both a length-wise and width-wise direction to facilitate conforming the undercast liner around the anatomical shape without wrinkling during application.

According to another embodiment of the invention, the yarn is selected from the group consisting of polypropylene, polyester, polyethylene and nylon.

According to another embodiment of the invention, liner is formed by one or more fabric-forming techniques selected from the group consisting of weaving, knitting non-woven, and stitching.

According to another embodiment of the invention, the fabric is treated with at least one finish for providing additional water resistance, anti-bacterial, anti-odor, or aromatherapy characteristics to improve the functionality of the liners or enhance the cast-wearing experience for the patient.

According to another embodiment of the invention, the liner includes an adhesive coating on at least one of the inner and outer faces to aid in application to the patient by adhering to itself and thus maintaining placement of partially overlying layers relative to each other as the liner is applied.

According to another embodiment of the invention, the liner has higher elongation in the width direction than in the length direction for allowing greater stretch during application.

According to another embodiment of the invention, the adhesive is preferably a low tack, pressure sensitive adhesive selected from the group consisting of acrylic and silicone adhesive.

According to another embodiment of the invention, the monofilament yarn has a diameter of at least 0.03 mm.

According to another embodiment of the invention, the monofilament yarn has a diameter of between approximately 0.05 and approximately 0.25 mm.

According to another embodiment of the invention, an undercast liner is provided, wherein the liner is constructed using a pillar and inlay stitch on the inner and outer faces and a needle V in the spacer area, and the yarn has a diameter of approximately 0.03 to approximately 0.25 mm. The liner is formed with at least 50 courses per meter and weighs between approximately 50 to approximately 400 grams per square meter.

According to another embodiment of the invention, the liner weighs between approximately 100 to approximately 250 grams per square meter and a nominal thickness when not compressed or under tension of approximately 1.5 to approximately 3.5 mm.

According to another embodiment of the invention, the liner includes a fluorochemical, silicone or other water repellant finish to improve drainage and provide faster drying.

According to another embodiment of the invention, an undercast liner for being applied to an anatomical shape of a patient and overlaid with a cast material is provided, and comprises a tubular fabric having two opposing faces and an intermediate spacer area that both separates and interconnects the opposed faces. The liner is constructed at least in part of hydrophobic, water resistant monofilament yarn for providing enhanced water resistance, light weight, breathability and resistance to collapse and degradation due to moisture and bacteria during extended use to the liner. The liner has sufficient stretch in both a length-wise and width-wise direction to facilitate conforming the undercast liner around the anatomical shape during application.

According to another embodiment of the invention, the liner includes a water repellant finish to improve drainage and provide faster drying.

According to another embodiment of the invention, an undercast liner for being applied to an anatomical shape of a patient and overlaid with a cast material is provided, and comprises an elongate fabric in roll form having two opposing faces and an intermediate spacer area that both separates and interconnects the opposed faces. The liner is constructed at least in part of hydrophobic, water resistant monofilament yarn for providing enhanced water resistance, light weight, breathability and resistance to collapse and degradation due to moisture and bacteria during extended use to the liner. The liner has sufficient stretch in both a length-wise and width-wise direction to facilitate conforming the undercast liner around the anatomical shape during application.

According to another embodiment of the invention, the monofilament yarn has a diameter of between approximately 0.05 and approximately 0.25 mm.

According to another embodiment of the invention, the liner is constructed using a pillar and inlay stitch on the inner and outer faces and a needle V in the spacer area. The yarn has a diameter of approximately 0.03 to approximately 0.25 mm, and the liner is formed with at least 50 courses per meter and weighs between approximately 50 to approximately 400 grams per square meter.

According to another embodiment of the invention, the liner weighs between approximately 100 to approximately 250 grams per square meter and has a nominal thickness when not compressed or under tension of approximately 1.5 to approximately 3.5 mm.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
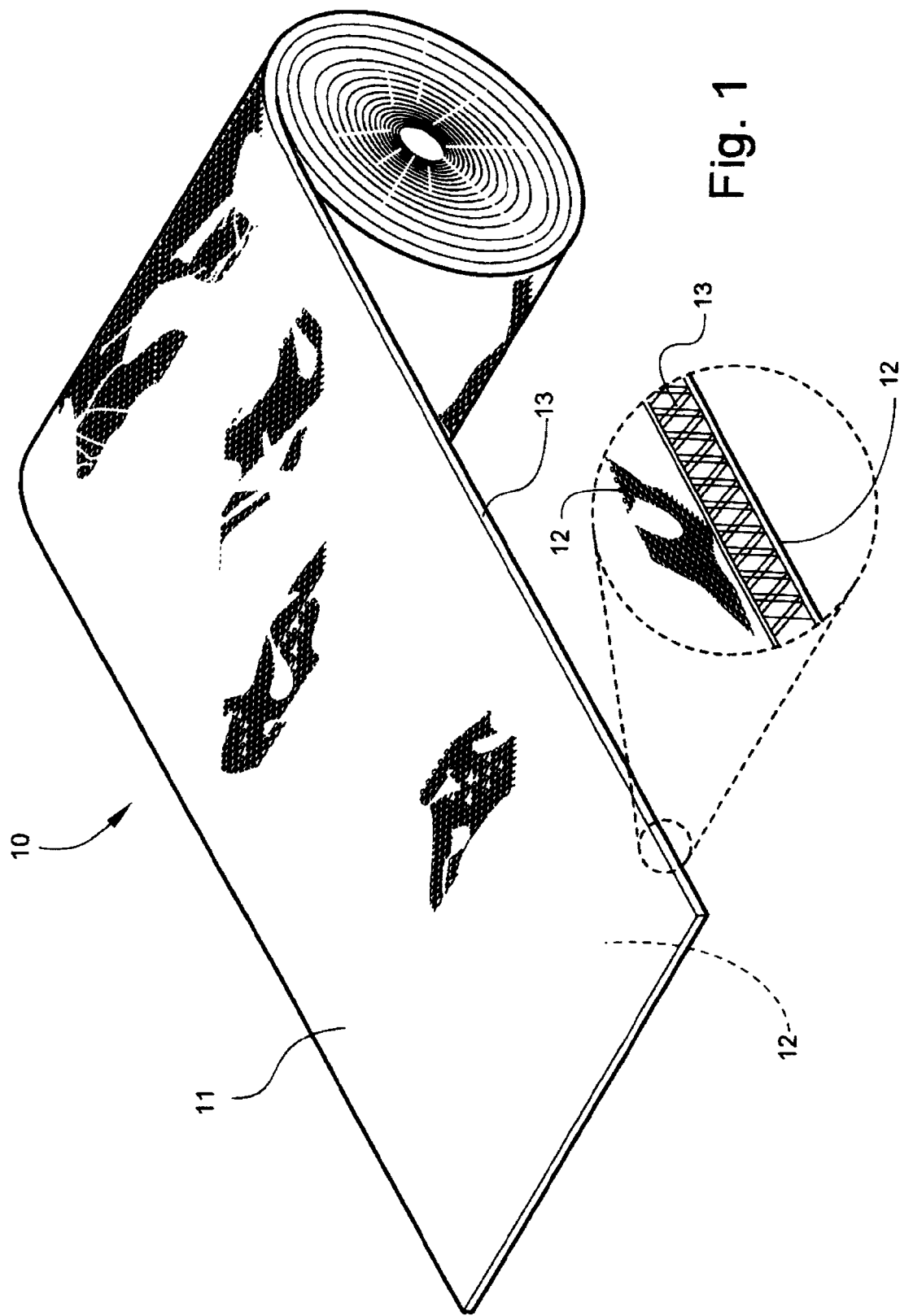
FIG. 1 is a perspective view of a roll of an undercast liner according to one embodiment of the invention.
Figure 2:
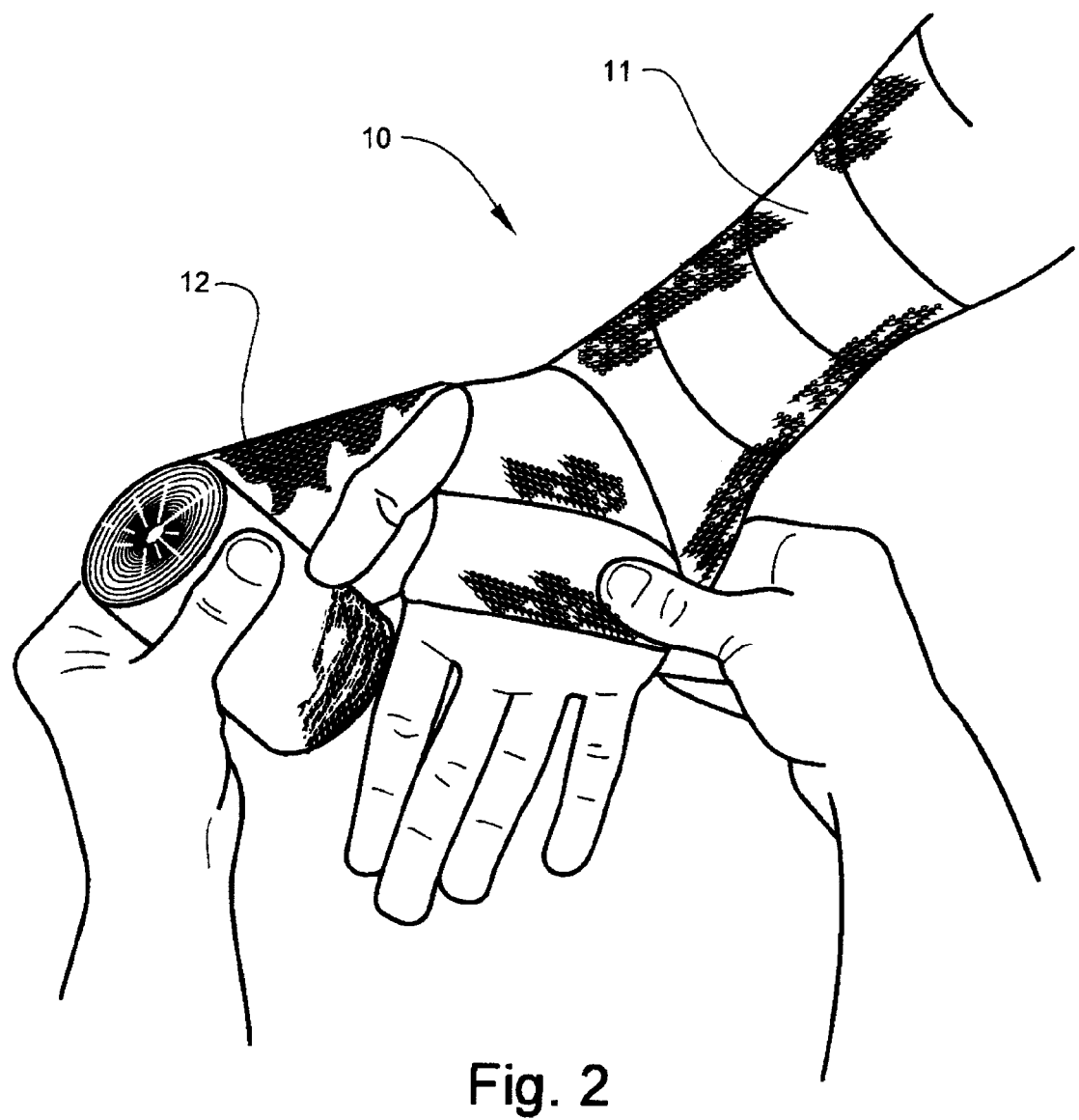
FIG. 2 is a view illustrating application of the undercast liner to the wrist and forearm.
Figure 3:
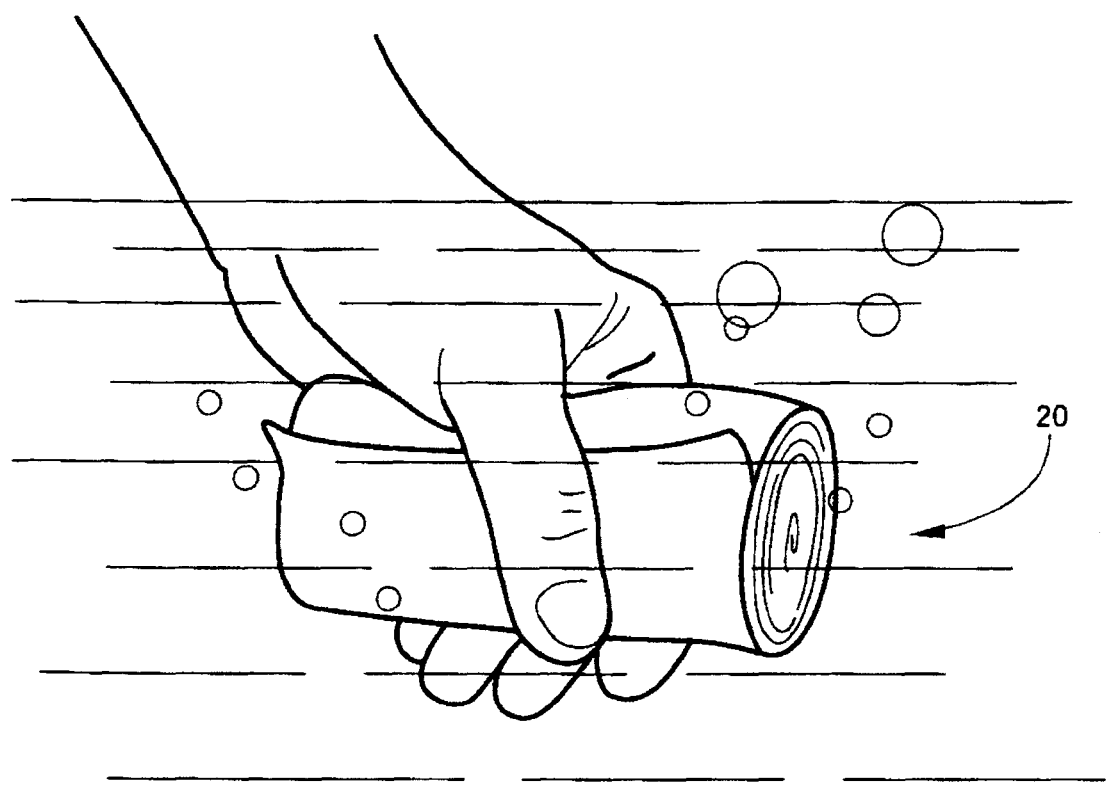
FIGS. 3 and 4 illustrate preparation of a cast tape for application over the undercast liner.

Referring now specifically to the drawings, a undercast liner according to the present invention is illustrated in FIG. 1 and shown generally at reference numeral 10. While the undercast liner 10 can be formed in any desired width or length, the undercast liner 10 shown in FIGS. 1, 2 and 3 is 7.5 cm (3 in.) wide and is formed into a roll during manufacture for shipping and storage until use. The undercast liner 10 is easily applied from the roll, as shown in FIG. 2. The liner 10 includes two opposing faces 11, 12 and an intermediate spacer area 13 that both separate and interconnect the faces 11, 12, as described in further detail below. The undercast liner 10 can be formed in a tubular form or in an elongate padding form in a roll.

The liner 10 can be constructed using any suitable organic or inorganic monofilament yarn, preferably a hydrophobic/water resistant monofilament yarn such as polypropylene, polyester, polyethylene and nylon. The monofilament yarn used for constructing the liner 10 preferably has a diameter of at least 0.03 mm. The liner 10 is constructed in a spacer fabric construction to provide sufficient cushioning and breathability, and it has been found that the use of a monofilament hydrophobic yarn on both faces 11, 12 and in the spacer area 13 provides enhanced water resistance, light weight, breathability and resistance to collapse and degradation due to moisture and bacteria during extended use.

The liner 10 is formed using any suitable fabric forming technology such as weaving, various knitting techniques such as, for example, weft knitting and warp knitting, non-woven, stitching or a combination of these techniques. Preferably, the structure should provide some stretch in both the length-wise and width-wise directions, and facilitate conforming the undercast liner 10 around an anatomical shape during application.

The liner 10 can be treated with one or more finishes to provide additional water resistance, anti-bacterial and/or anti-odor characteristics, or aromatherapy to improve the functionality or enhance the cast-wearing experience for the patient. Alternatively, the liner 10 can be fabricated from modified/treated monofilament yarns incorporating suitable fillers or finishes to improve the performance of the liner 10.

The liner 10 may also be provided with an adhesive coating on one or both faces 11, 12 to aid in application to the patient. The adhesive is preferably any suitable low tack, pressure sensitive adhesive, such as an acrylic or silicone adhesive. The adhesive aids in application by adhering to itself and thus maintaining the exact placement of the layers relative to each other as the liner 10 is applied by the cast technician.

In one preferred embodiment, the liner 10 is constructed as a spacer fabric using polypropylene monofilament and a low tack, pressure sensitive adhesive on one surface. The monofilament yarn has a diameter of at least 0.03 mm, and preferably between 0.05-0.25 mm. Preferably, the liner 10 requires no additional finish or water repellency treatment.

More specifically, the preferred embodiment of the liner 10 is constructed of a polypropylene monofilament yarn on a double needle bed knitting machine, and can be knitted on either a warp knitting Raschel machine or a Crochet knitting machine. The liner 10 is preferably constructed using a pillar and inlay stitch on the surfaces 11, 12 and a 3 or 5 needle V in the spacer area 13. The yarn has a diameter of 0.03-0.25 mm. The fabric for the liner 10 is formed with at least 50 courses per meter preferably 200-850 courses per meter. The liner 50 weighs between 50-400 grams per square meter, and more preferably between 100-250 grams per square meter. The liner 10 has a nominal thickness when not compressed or under tension of approximately 1.5-3.5 mm.

Alternatively, an undercast liner may be constructed as a spacer fabric with at least one of the yarns being a multifilament or spun yarn in order to provide even more patient comfort. The liner may be treated with suitable fluorochemical, silicone or other water repellant finish to improve drainage and provide faster drying.

Referring now to FIG. 2, the undercast liner 10 is applied to the injured limb in a conventional manner. As noted above, the stretch provided by the undercast liner 10 permits a fast, accurate, closely-conforming application without wrinkles or creases.

Figure 4:
Figure 5:
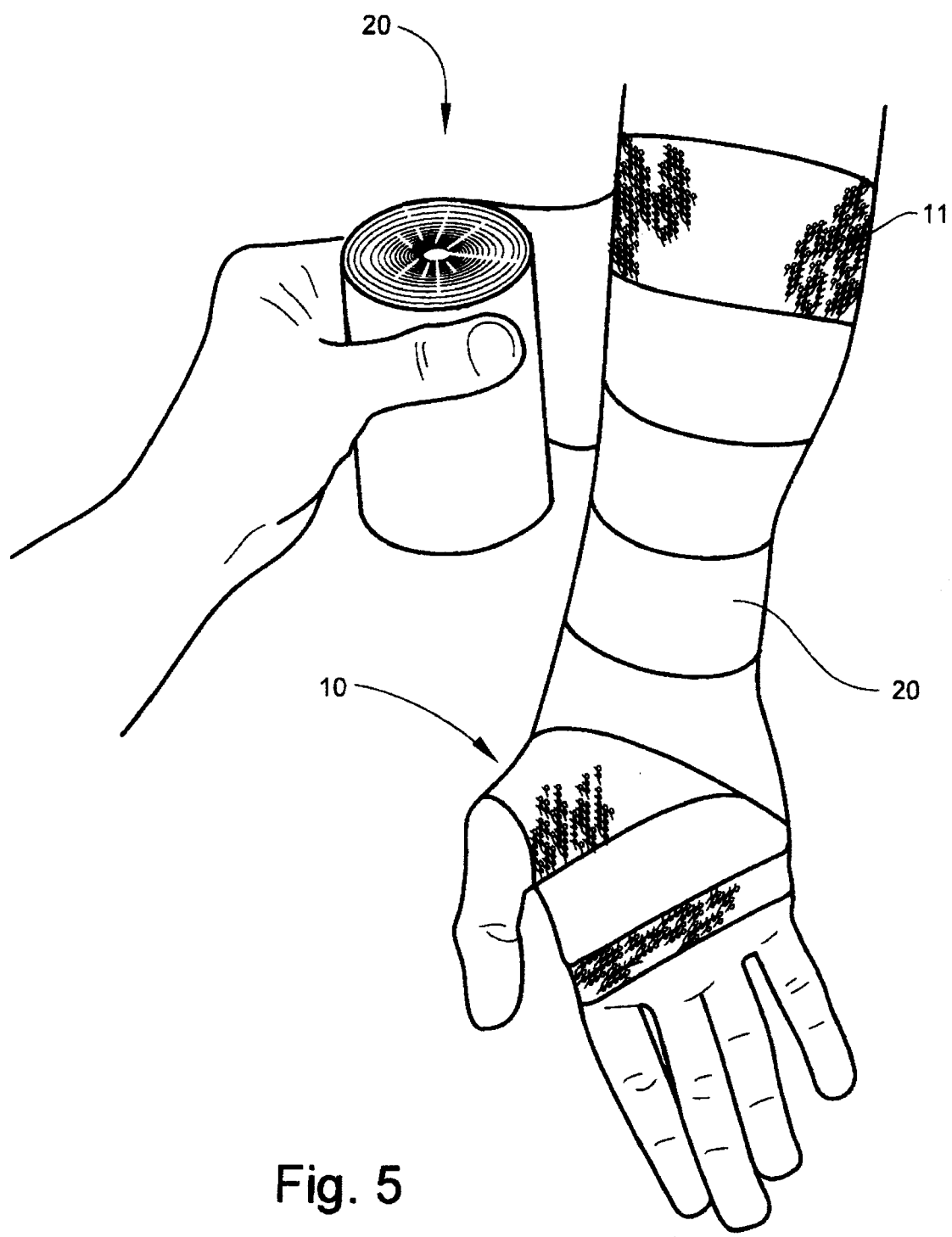
FIGS. 5 and 6 illustrate application of the cast tape to the undercast liner.
Figure 6:
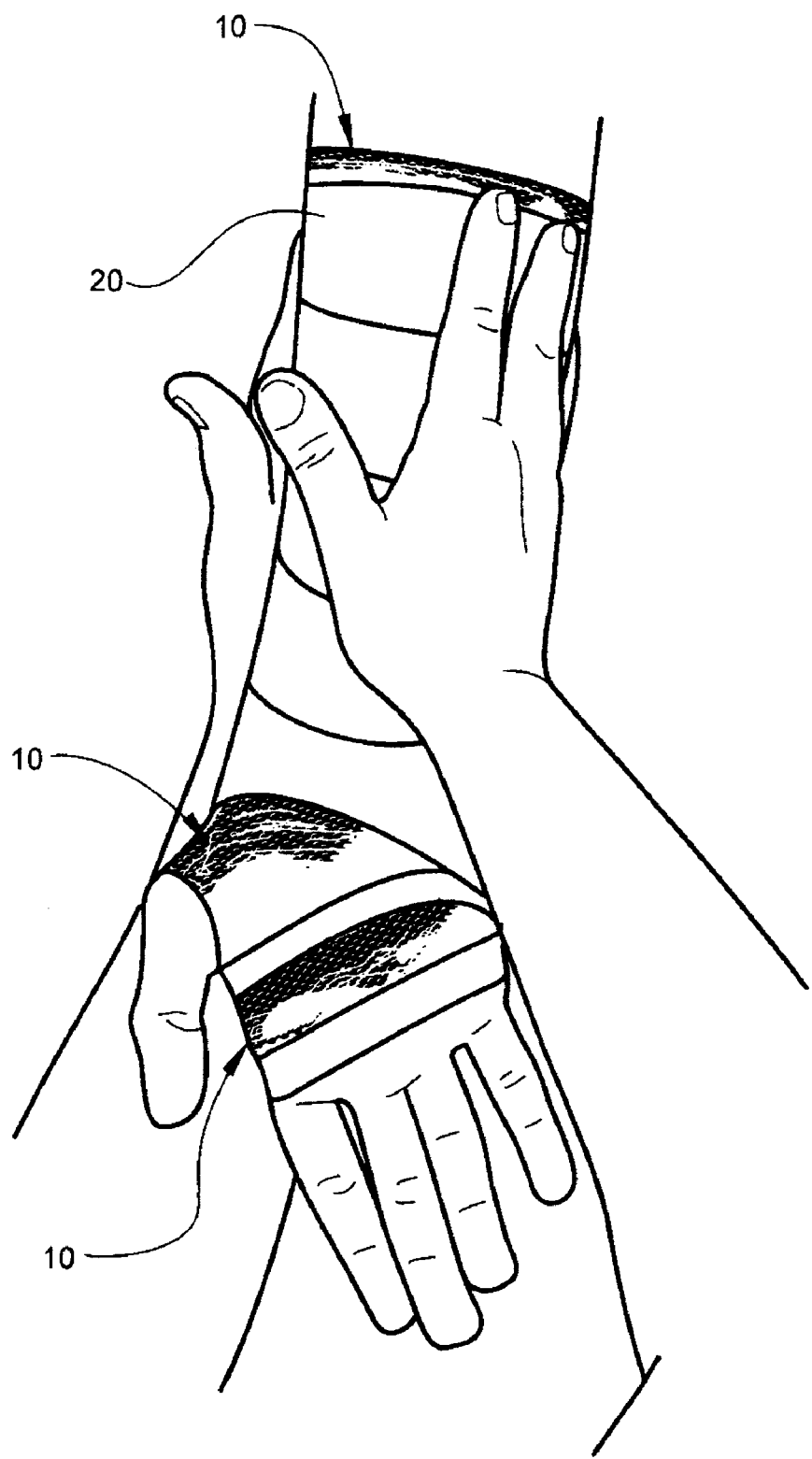
Figure 7:
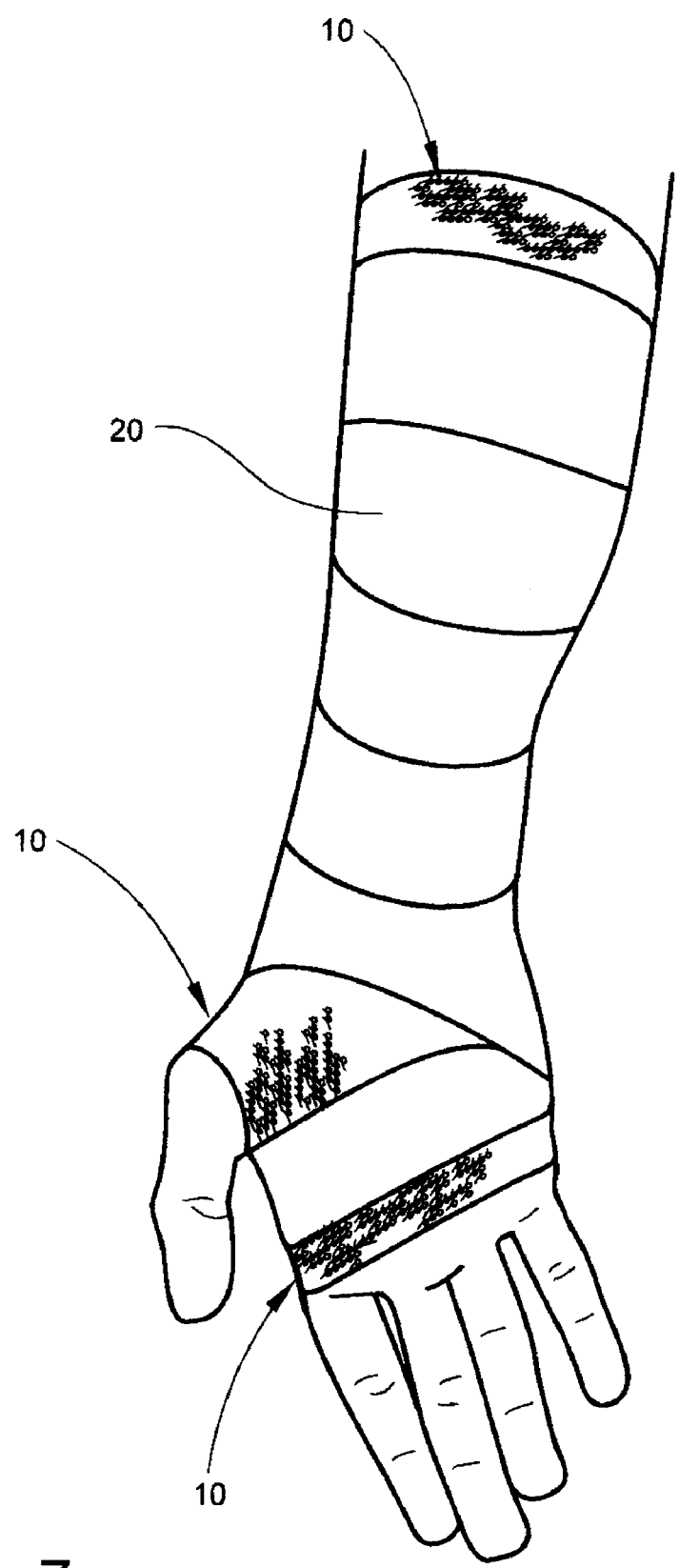
FIG. 7 illustrates the completed cast.

As is shown in FIGS. 3-7, after application of the undercast liner 10, a conventional cast tape 20 is wetted, FIG. 3, excess water removed by wringing, FIG. 4, and applied to the injured limb, FIGS. 5-7, taking care in the usual manner to avoid overlapping the undercast liner 10 on opposite ends, leaving a short width of exposed undercast liner 10.

Figure 8:
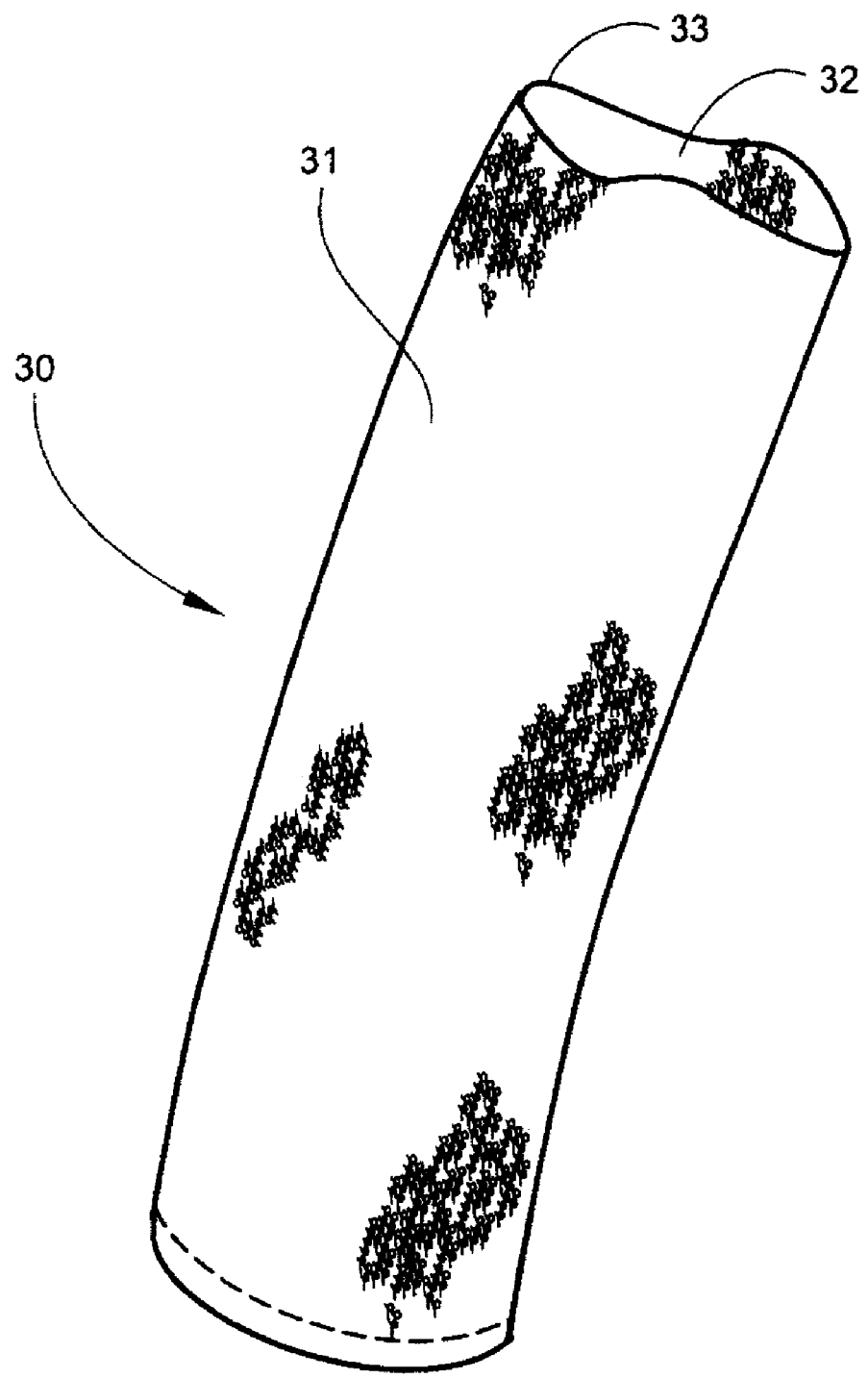
FIG. 8 illustrates a liner in the form of a circular sleeve.
Figure 9:
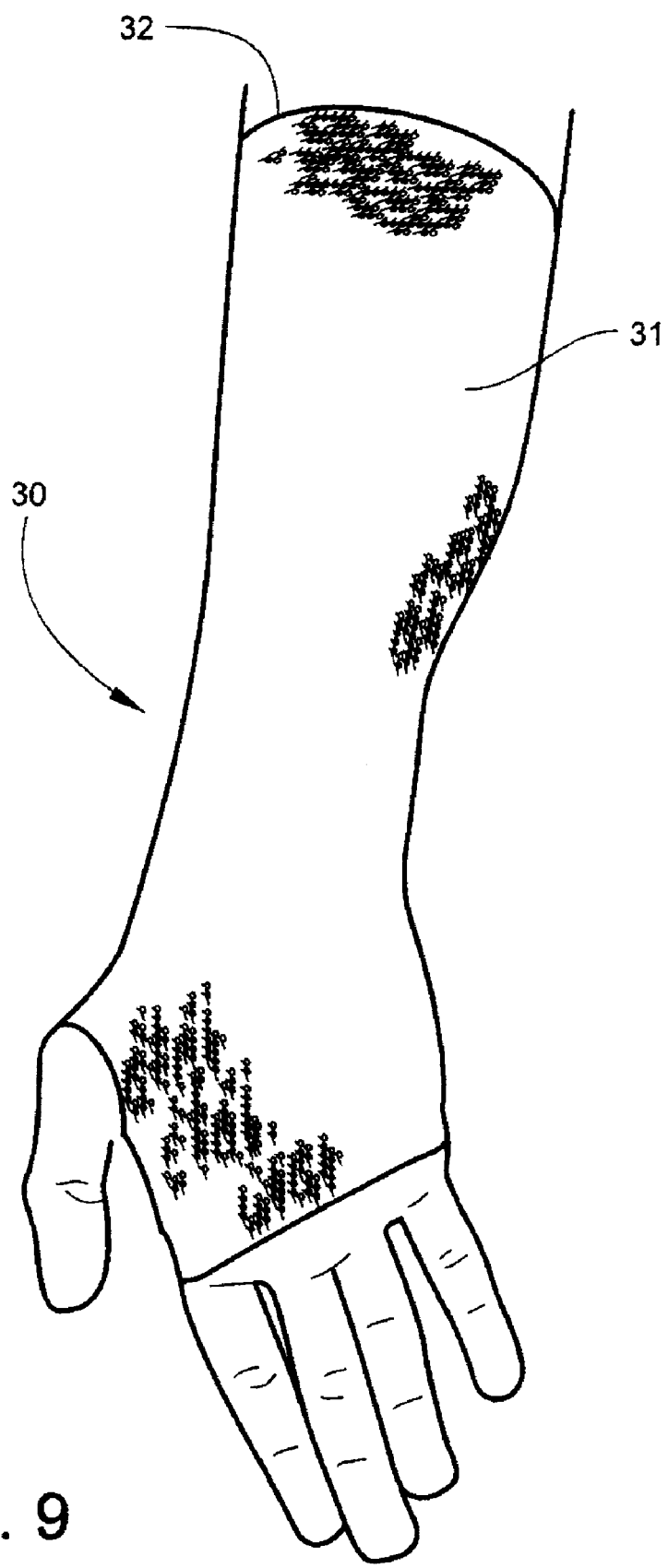
FIG. 9 shows the sleeve in place on an arm prior to application of a cast tape bandage.

Referring now to FIG. 8, a circular knit liner 30 is shown, preferably with the same preferred constructions described above. The liner 30 includes an outer face 31, an inner face 32 and a spacer area 33 that both separates and interconnects the two faces 31, 32, as shown in FIG. 1. Instead of wrapping, the liner 30 is pulled onto the limb as shown in FIG. 9, in the same manner as a conventional stockinette. Thereafter, a cast tape 20 is applied in a conventional manner.

An undercast liner is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. An undercast liner for being applied to an anatomical shape of a patient and overlaid with a cast material, comprising:
an integrated, woven fabric including inner and outer opposing faces constructed of pillar and inlay stitches interconnected and separated by an intermediate spacer area having a needle V stitch construction, all of the inner and outer opposing faces and the spacer area consisting of hydrophobic monofilament yarn, and the liner having a thickness of at least about 1.5 mm.

2. An undercast liner according to claim 1, wherein the liner includes an adhesive coating on at least one of the inner and outer faces to aid in application to the patient by adhering to itself and thus maintaining placement of partially overlying layers relative to each other as the liner is applied.

3. An undercast liner according to claim 2, wherein the adhesive is preferably a low tack, pressure sensitive adhesive selected from the group consisting of acrylic and silicone adhesive.

4. An undercast liner according to claim 1, wherein the hydrophobic monofilament yarn is selected from the group consisting of polypropylene, polyester, polyethylene and nylon.

5. An undercast liner according to claim 1, wherein the fabric is treated with at least one finish for providing additional water resistance, anti-bacterial, anti-odor, or aromatherapy characteristics to improve the functionality of the liners or enhance the cast-wearing experience for the patient.

6. An undercast liner according to claim 1, wherein the liner has higher elongation in the width direction than in the length direction for allowing greater stretch during application.

7. An undercast liner according to claim 1, wherein the hydrophobic monofilament yarn has a diameter of at least 0.03 mm.

8. An undercast liner according to claim 1, wherein the hydrophobic monofilament yarn has a diameter of between approximately 0.05 and approximately 0.25 mm.

9. An undercast liner according to claim 1, wherein the hydrophobic monofilament yarn has a diameter of approximately 0.03 to approximately 0.25 mm; and the liner is formed with at least 50 courses per meter and weighs between approximately 50 to approximately 400 grams per square meter.

10. An undercast liner according to claim 1, wherein the liner weighs between approximately 100 to approximately 250 grams per square meter and a nominal thickness when not compressed or under tension of approximately 1.5 to approximately 3.5 mm.

11. An undercast liner according to claim 1, wherein the liner includes a fluorochemical, silicone or other water repellant finish to improve drainage and provide faster drying.

* * * * *